US005726148A

United States Patent [19]

Katoh et al.

[11] Patent Number: 5,726,148
[45] Date of Patent: Mar. 10, 1998

[54] METHOD OF TREATING METABOLIC BONE DISEASES WITH AN IL-1 RECEPTOR

[75] Inventors: Masakazu Katoh, Hiki-gun; Kazuyuki Kitamura, Sakado, both of Japan

[73] Assignee: Hoechst Japan Limited, Tokyo, Japan

[21] Appl. No.: 487,646

[22] Filed: Jun. 7, 1995

[30] Foreign Application Priority Data

Jun. 11, 1994 [JP] Japan ................................. 6-135275

[51] Int. Cl.⁶ ................................................ A61K 45/05
[52] U.S. Cl. ................................ 514/2; 514/8; 514/12; 424/85.2
[58] Field of Search ................... 514/2, 8, 12; 424/85.2

[56] References Cited

U.S. PATENT DOCUMENTS

| 5,180,812 | 1/1993 | Dower et al. ........................... 530/351 |
| 5,319,071 | 6/1994 | Dower et al. ........................... 435/69.1 |

FOREIGN PATENT DOCUMENTS

| 0 318 296 A3 | 5/1989 | European Pat. Off. . |
| 0 474 141 A1 | 3/1992 | European Pat. Off. . |
| 91 00742 | 1/1991 | WIPO . |
| 92 11359 | 7/1992 | WIPO . |

OTHER PUBLICATIONS

M. Tanihara et al., "A Synthetic Peptide Corresponding to 86–93 of the Type I IL–1 Receptor Binds Human Recombinant IL–1 ($\alpha$ and $\beta$) and Inhibits IL–1 Actions in Vitro and in Vivo", Biochem. Biophys. Res. Comm., vol. 188, No. 2, Oct. 30, 1992, pp. 912–920.

S.K. Dower et al., "Retention of Ligand Binding Activity By the Extracellular Domain of the IL–1 Receptor", J. Immunology, vol. 142, No. 12 Jun. 15, 1989, pp. 4314–4320.

C.R. Maliszewski et al., "Cytokine Receptors and B Cell Functions: I. Recombinant Soluble Receptors Specifically Inhibit IL–1–and IL–4–Induced B Cell Activities in Vitro," Journal of Immunology, vol. 144, No. 8, Apr. 15, 1990, pp. 3028–3033.

P. Seckinger et al., "Natural and Recombinant Human IL–1 Receptor Antagonists Block the Effects of IL–1 on Bone Resorption and Prostaglandin Production", Journal of Immunology, vol. 145, No. 12, Dec. 15, 1990, pp. 4181–4184.

M. Gowen et al., Nature, vol. 306 (1983) pp. 378–381.

J. Pfeilschifter et al., J. of Bone and Mineral Res., vol. 4, No. 1 (1989) pp. 113–118.

B.M. Thomson et al., J. Exp. Med. (1986) pp. 104–112.

Gershenwald et al *PNAS* 87, 1990, pp. 966–970.

Fanslow et al *Science* 248, 1990, pp. 739–742.

Cominelli et al *J. Clin. Invest* 86, 1990, pp. 972–980.

*Primary Examiner*—Garnette D. Draper
*Attorney, Agent, or Firm*—Finnegan, Henderson, Farabow, Garrett & Dunner, L.L.P.

[57] ABSTRACT

A method of treating metabolic bone diseases comprising using a pharmaceutical composition which comprises as an active ingredient IL-1 receptor, a soluble fragment consisting of an extracellular domain of IL-1R or a fragment thereof derived from mammals. The composition has a bone resorption inhibiting activity and is useful for the therapy and prophylaxis of metabolic bone diseases.

7 Claims, No Drawings

1

METHOD OF TREATING METABOLIC BONE DISEASES WITH AN IL-1 RECEPTOR

BACKGROUND OF THE INVENTION

1. Field of the Invention

This invention relates to a pharmaceutical composition for preventing and curing the diseases which are caused by abnormal decrease of calcium and bone matrix from bone.

2. Description of the Prior Art

Abnormal bone resorption is caused by, not to speak of osteoporosis, rheumatoid arthritis, Paget's disease, metastasis of malignant tumors to bone, hyperthyroidism, postovariectomy, and moreover, appendicular neurectomy, or disuse or fixation for a long time. As a result, a bone strength decreases and a risk of bone fracture increases. Furthermore, a prolongation in a short period of average span of human life leads to an increase in population of elders over 65 years old, and an increase in the number of patients with the afore-mentioned diseases, especially osteoporosis, is estimated. The medicaments so far applied clinically are vitamin $D_3$, calcitonin, estrogen, bisphosphonate derivatives and the like. However, a treatment with these medicaments is not considered satisfactory, and therefore a distinctly superior therapeutic agent has been desired.

DETAILED DESCRIPTION OF THE INVENTION

Thus, an object of the invention is to provide a novel pharmaceutical composition having an excellent therapeutic effect for metabolic bone diseases.

Bone resorption is known to be caused by activation of osteoclasts. Also, interleukin 1 (IL-1 hereinafter) is known to activate osteoclasts and, thus, induce bone resorption (Gowen et al., Nature, vol. 306, p. 378–380, 1983; Pfeilschifter et al., J. Bone Miner. Res., vol. 4, p. 113–118, 1989; Thomson et al., J. Exp. Med., vol. 164, p. 104–112, 1989). The present inventors postulated that some inhibitors to IL-1 inhibit bone resorption, and have found, as a result of various studies, that IL-1 receptor (IL-1R hereinafter), soluble IL-1R which consists of an extracellular domain of IL-1R and the fragment thereof inhibited bone resorption, and successfully completed the invention. Incidentally, some inhibitors to IL-1 have already been reported to inhibit bone resorption, such as IL-1 receptor antagonist (IL-1ra hereinafter) by Seckinger et al. (J. Immunology, vol. 145, p. 4181–4184, 1990) and a synthetic peptide of amino acid sequence 86–93 of IL-1R type-I by Tanihara et al. (Biochem. Biophys. Res. Commun., vol. 188, p. 912–920, 1992; Japanese Patent Kokai No. 9199/1993). However, IL-1ra is known to be produced in a body, and the effect of an agent containing IL-1ra may be affected by the endogenous IL-1ra. In addition, the affinity of synthetic peptide of IL-1R to IL-1 is very low. The present invention has already solved the above-mentioned problems, and therefore the pharmaceutical composition according to the invention is highly expected to have an excellent bone resorption inhibitory activity.

IL-1R according to the present invention exists in the body of mammals such as human, monkey, mouse and the like. Particularly preferred human IL-1R is composed of 569 amino acids shown in SEQ ID No.:1 of the Sequence Listing, preferably a soluble fragment keeping its physiological activity. A preferable example of the soluble fragment is a protein comprising an amino acid sequence 1–319 in SEQ ID No.:1 of the Sequence Listing, and more preferably a soluble protein comprising an amino acid sequence 1–312 (shuIL-1R hereinafter). The shuIL-1R is a known protein disclosed in Japanese Patent Kokai No. 332994/1993. IL-1R type-I and the soluble fragment thereof can be purified from leukocytes of mammals, however, it is more desirable to produce them by a gene engineering method as described in the afore-mentioned publication.

The protein according to the present invention is useful as a bone resorption inhibiting agent, and it can be administered intravenously and intramuscularly. In case of intravenous administration, an intravenous drip can be used, in addition to usual intravenous injections.

Injectable preparations can be formulated, for example, in the form of injectable powders. In that case, the powders can be prepared by adding one or more of suitable excipients such as mannitol, sucrose, lactose, maltose, glucose, fructose and the like, to an active ingredient, dissolving the mixture in water, dividing it into vials or ampoules followed by lyophilizing and hermetically sealing. The dosage in clinical use is normally within a range of 1–500 µg as shuIL-1R per adult per day, though it varies depending on administration method, patient's age, body weight and symptoms.

Bone resorption inhibitory activity of the protein according to the present invention has been proved by assaying a direct action on osteoclast activity, for example, by pit formation assay. According to the assay, osteoclasts dissolve bone tissues on ivory slices to form resorbed lacunae (pits) when the mouse parathyroid hormone (PTH hereinafter) long bone cell suspension containing osteoclasts is cultivated on ivory slices. Osteoclasts are further activated by addition of IL-1 to the test suspension, and the number of resorbed lacunae increases. The protein according to the present invention is added thereto, and the effect of the protein can be assayed by counting the number of pits on ivory slices formed by osteoclasts. The higher the bone resorption inhibitory effect becomes, the smaller the number of counted pits becomes.

The effects of the invention shall be illustratively explained by the following examples.

EXAMPLES

Example 1

Preparation of mouse long bone cells

The femur, tibia and fibula of 10-day-old ICR mice (purchased from Charles River Inc.) were aseptically removed and dissected free of adhering tissue. Bone fragments were released by mincing the bones in α-MEM (α-Modified Eagle's Medium) supplemented with 5% FCS (fetal calf serum). After the removal of larger bone fragments by sedimentation in 3 minutes, the suspended cells were recovered from the supernatant, centrifuged at 1,200 rpm for 5 minutes and a fresh medium was added to the precipitate. The resultant cells were washed once and resuspended in FCS-α-MEM supplemented with PTH ($10^{-8}$M). These prepared long bone cells were then cultured in 75 cm$^2$ culture flasks at a concentration of about $5 \times 10^6$ cells/ml, and 15 ml of the prepared cells/flask were maintained for 7 days at 37° C. in a 5% $CO_2$ incubator; the culture medium was replaced with fresh medium containing PTH ($10^{-8}$M) after 3 days. After cultivation with PTH, activated long bone cells (PTH-psLB cells) were harvested using trypsin-EDTA and a cell scraper and then resuspended in 5% FCS-α-MEM.

Example 2

Bone resorption inhibitory activity in vitro of a soluble IL-1 receptor type-I

The mouse PTH long bone cells obtained in Example 1 was adjusted to a concentration of $1 \times 10^6$ cells/ml. One hundred microliters of 5% FCS-α-MEM with 1 ng/ml of human IL-1α or human IL-1β (purchased from Genzyme Co.), containing shuIL-1R at the various concentrations between 0.01 and 10 μg/ml, was added on 96-well culture plate placed with ivory slices (6 mm in diameter), and 100 μl of the PTH-psLB cell suspension was overlaid onto each well. The plates were then incubated for 48 hours at 37° C. in a humidified atmosphere of 5% $CO_2$ incubator. After the incubation, resorbed lacunae on each ivory slice were stained with Coomassie Brilliant Blue and the number of resorbed lacunae (pits) was counted under a light microscope. The number of resorbed lacunae (pits) in the medicament-added and non-added groups is evaluated by student-t assay. Hereupon, shuIL-1 was prepared by expressing, in mouse myeloma cells, a DNA sequence encoding a protein consisting of the amino acid sequence 1–312 in SEQ ID No.:1 of the Sequence Listing as shown in FIG. 1 according to the method disclosed in Example 4 of Japanese Patent Kokai No. 332994/1993. The results are shown in Table 1.

TABLE

| Medicament | Medicament conc. (ng/ml) | IL-1 | Number of Resorbed Iacunae |
|---|---|---|---|
| Control | 0 | 0 | 654.3 ± 156.0 |
| shuIL-1R | 0.01 | 0 | 655.5 ± 107.5 |
| shuIL-1R | 0.1 | 0 | 527.8 ± 189.1 |
| shuIL-1R | 1 | 0 | 566.0 ± 160.9 |
| shuIL-1R | 10 | 0 | 592.0 ± 179.2 |
| Control + hIL-1α | 0 | hIL-1α(1 ng/ml) | 1578.3 ± 103.8 |
| shuIL-1R | 0.01 | hIL-1α(1 ng/ml) | 1555.5 ± 219.5 |
| shuIL-1R | 0.1 | hIL-1α(1 ng/ml) | 1552.8 ± 95.1 |
| shuIL-1R | 1 | hIL-1α(1 ng/ml) | 1139.8 ± 95.7* |
| shuIL-1R | 10 | hIL-1α(1 ng/ml) | 663.5 ± 175.1* |
| Control + hIL-1β | 0 | hIL-1β(1 ng/ml) | 1032.8 ± 170.9 |
| shuIL-1R | 0.01 | hIL-1β(1 ng/ml) | 1031.0 ± 134.8 |
| shuIL-1R | 0.1 | hIL-1β(1 ng/ml) | 1024.5 ± 131.8 |
| shuIL-1R | 1 | hIL-1β(1 ng/ml) | 776.5 ± 137.6* |
| shuIL-1R | 10 | hIL-1β(1 ng/ml) | 667.0 ± 74.1* |

Mean ± standard deviation, *: $p < 0.01$ (vs corresponding control)

As shown in the above Table, shuIL-1R reduced the number of resorbed lacunae increased by hIL-1α or hIL-1β at 1 ng/ml. Moreover, 10 ng/ml of shuIL-1R did not show any inhibitory effect without IL-1, which indicated that the inhibitory activity of shuIL-1R was specific for IL-1.

Accordingly, shuIL-1R was confirmed to inhibit bone resorption and expected to be utilized as an active ingredient of a pharmaceutical composition for treating metabolic bone diseases caused by bone resorption, such as osteoporosis and hypercalcemia.

What is claimed is:

1. A method of treating metabolic bone diseases caused by abnormal bone resorption associated with IL-1, comprising administering to a patient in need of such treatment an effective amount of a pharmaceutical composition which comprises as an active ingredient the full length of human IL-1 receptor as identified by SEQ ID NO:1 or the soluble fragment of human IL-1 receptor comprising amino acids 1 to 312 of SEQ ID NO:1.

2. The method of treating metabolic bone diseases as claimed in claim 1, wherein the diseases arise from bone resorption.

3. The method of treating metabolic bone diseases as claimed in claim 1, wherein the diseases arise from IL-1.

4. The method of treating metabolic bone diseases as claimed in claim 1, comprising administering a soluble fragment of IL-1 receptor.

5. The method of claim 4, wherein the soluble fragment of IL-1 receptor is a soluble fragment of human IL-1 receptor.

6. The method of claim 5 wherein the soluble fragment of human IL-1 receptor is a soluble fragment of human IL-1 receptor type-1.

7. The method of claim 6, wherein the human IL-1 receptor type-1 is composed of the amino acid sequence 1–312 in SEQ ID No.:1 of the Sequence Listing.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 569 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Met Lys Val Leu Leu Arg Leu Ile Cys Phe Ile Ala Leu Leu Ile Ser
 1               5                  10                  15

Ser Leu Glu Ala Asp Lys Cys Lys Glu Arg Glu Glu Lys Ile Ile Leu
                20                  25                  30

Val Ser Ser Ala Asn Glu Ile Asp Val Arg Pro Cys Pro Leu Asn Pro
            35                  40                  45

Asn Glu His Lys Gly Thr Ile Thr Trp Tyr Lys Asp Asp Ser Lys Thr
        50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
               100                 105                 110

Phe Val Glu Asn Glu Pro Asn Leu Cys Tyr Asn Ala Gln Ala Ile Phe
```

-continued

```
            115                         120                         125
Lys Gln Lys Leu Pro Val Ala Gly Asp Gly Gly Leu Val Cys Pro Tyr
            130                     135                 140
Met Glu Phe Phe Lys Asn Glu Asn Asn Glu Leu Pro Lys Leu Gln Trp
145                     150                     155                     160
Tyr Lys Asp Cys Lys Pro Leu Leu Leu Asp Asn Ile His Phe Ser Gly
                    165                     170                     175
Val Lys Asp Arg Leu Ile Val Met Asn Val Ala Glu Lys His Arg Gly
                180                     185                     190
Asn Tyr Thr Cys His Ala Ser Tyr Thr Tyr Leu Gly Lys Gln Tyr Pro
            195                     200                     205
Ile Thr Arg Val Ile Glu Phe Ile Thr Leu Glu Glu Asn Lys Pro Thr
210                     215                     220
Arg Pro Val Ile Val Ser Pro Ala Asn Glu Thr Met Glu Val Asp Leu
225                     230                     235                 240
Gly Ser Gln Ile Gln Leu Ile Cys Asn Val Thr Gly Gln Leu Ser Asp
                    245                     250                     255
Ile Ala Tyr Trp Lys Trp Asn Gly Ser Val Ile Asp Glu Asp Asp Pro
                260                     265                     270
Val Leu Gly Glu Asp Tyr Tyr Ser Val Glu Asn Pro Ala Asn Lys Arg
            275                     280                     285
Arg Ser Thr Leu Ile Thr Val Leu Asn Ile Ser Glu Ile Glu Ser Arg
        290                     295                     300
Phe Tyr Lys His Pro Phe Thr Cys Phe Ala Lys Asn Thr His Gly Ile
305                     310                     315                 320
Asp Ala Ala Tyr Ile Gln Leu Ile Tyr Pro Val Thr Asn Phe Gln Lys
                    325                     330                     335
His Met Ile Gly Ile Cys Val Thr Leu Thr Val Ile Ile Val Cys Ser
                340                     345                     350
Val Phe Ile Tyr Lys Ile Phe Lys Ile Asp Ile Val Leu Trp Tyr Arg
            355                     360                     365
Asp Ser Cys Tyr Asp Phe Leu Pro Ile Lys Ala Ser Asp Gly Lys Thr
        370                     375                     380
Tyr Asp Ala Tyr Ile Leu Tyr Pro Lys Thr Val Gly Glu Gly Ser Thr
385                     390                     395                 400
Ser Asp Cys Asp Ile Phe Val Phe Lys Val Leu Pro Glu Val Leu Glu
                    405                     410                     415
Lys Gln Cys Gly Tyr Lys Leu Phe Ile Tyr Gly Arg Asp Asp Tyr Val
                420                     425                     430
Gly Glu Asp Ile Val Glu Val Ile Asn Glu Asn Val Lys Lys Ser Arg
            435                     440                     445
Arg Leu Ile Ile Ile Leu Val Arg Glu Thr Ser Gly Phe Ser Trp Leu
450                     455                     460
Gly Gly Ser Ser Glu Glu Gln Ile Ala Met Tyr Asn Ala Leu Val Gln
465                     470                     475                 480
Asp Gly Ile Lys Val Val Leu Leu Glu Leu Glu Lys Ile Gln Asp Tyr
                    485                     490                     495
Glu Lys Met Pro Glu Ser Ile Lys Phe Ile Lys Gln Lys His Gly Ala
                500                     505                     510
Ile Arg Trp Ser Gly Asp Phe Thr Gln Gly Pro Gln Ser Ala Lys Thr
            515                     520                     525
Arg Phe Trp Lys Asn Val Arg Tyr His Met Pro Val Gln Arg Arg Ser
530                     535                     540
```

-continued

```
Pro  Ser  Ser  Lys  His  Gln  Leu  Leu  Ser  Pro  Ala  Thr  Lys  Glu  Lys  Leu
545                      550                 555                           560

Gln  Arg  Glu  Ala  His  Val  Pro  Leu  Gly
                    565
```